United States Patent
Wei et al.

(10) Patent No.: US 6,583,875 B1
(45) Date of Patent: Jun. 24, 2003

(54) MONITORING TEMPERATURE AND SAMPLE CHARACTERISTICS USING A ROTATING COMPENSATOR ELLIPSOMETER

(75) Inventors: Lanhua Wei, Fremont, CA (US); Jon Opsal, Livermore, CA (US); Allan Rosencwaig, Danville, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 09/575,295

(22) Filed: May 19, 2000

(51) Int. Cl.$^7$ ................................................. G01J 4/00
(52) U.S. Cl. ......................................................... 356/369
(58) Field of Search .......................... 356/369, 364–368; 250/225, 227.17, 252.1

(56) References Cited

U.S. PATENT DOCUMENTS

| | | | | |
|---|---|---|---|---|
| 5,311,284 A | * | 5/1994 | Nishino | 356/364 |
| 5,877,859 A | | 3/1999 | Aspnes et al. | 356/364 |
| 6,278,519 B1 | * | 8/2001 | Rosencwaig et al. | 356/369 |
| 6,449,043 B2 | * | 9/2002 | Aspnes et al. | 356/369 |
| 6,473,179 B1 | * | 10/2002 | Wang et al. | 356/364 |
| 6,483,585 B1 | * | 11/2002 | Yang | 356/369 |

FOREIGN PATENT DOCUMENTS

| WO | WO 97/35177 | 9/1997 | G01N/21/21 |
|---|---|---|---|
| WO | WO 99/02970 | 1/1999 | G01N/21/21 |

OTHER PUBLICATIONS

R.K. Sampson et al., "Simultaneous Silicon Wafer Temperature and Oxide Film Thickness Measurement in Rapid–Thermal Processing Using Ellipsometry," *J. Electrochem. Soc.*, Vol. 140, No. 6, Jun. 1993, pp. 1734–1743.

G.M.W. Kroesen et al., "Nonintrusive wafer temperature measurement using in situ ellipsometry," *J. Appl. Phys.*, vol. 69, No. 5, Mar. 1, 1991, pp. 3390–3392.

K.A. Conrad et al., "Ellipsometric Monitoring and control of the rapid thermal oxidation of silicon," *J. Vac. Sci. Technol. B*, vol. 11, No. 6, Nov./Dec. 1993, pp. 2096–2101.

* cited by examiner

*Primary Examiner*—Frank G. Font
*Assistant Examiner*—Layla Lauchman
(74) *Attorney, Agent, or Firm*—Stallman & Pollock LLP

(57) ABSTRACT

An method and apparatus are disclosed for accurately and repeatably determining the thickness of a thin film on a substrate. A rotating compensator ellipsometer is used which generates both $2\omega$ and $4\omega$ output signals. The $4\omega$ omega signal is used to provide an indication of the temperature of the sample. This information is used to correct the analysis of the thin film based on the $2\omega$ signal. These two different signals generated by a single device provide independent measurements of temperature and thickness and can be used to accurately analyze a sample whose temperature is unknown.

11 Claims, 3 Drawing Sheets

MONITORING TEMPERATURE AND SAMPLE CHARACTERISTICS USING A ROTATING COMPENSATOR ELLIPSOMETER

TECHNICAL FIELD

The subject invention relates to evaluating samples using a rotating compensator ellipsometer. More specifically, the rotating compensator ellipsometer is utilized to monitor simultaneously and independently sample characteristics, in particular temperature and oxide thickness.

BACKGROUND OF THE INVENTION

There is considerable interest in the semiconductor industry in optically monitoring wafers during the fabrication process. Various metrology tools have been developed to characterize thin film layers formed on silicon substrates. Parameters of particular interest include thin film thickness, index of refraction and extinction coefficient.

Recently, a need has developed for measuring very thin gate dielectrics. These gate dielectric layers are typically only about 20 angstroms thick. In order to measure these layers accurately, very stable and repeatable systems are necessary.

One difficulty associated with measuring such thin layers relates to errors associated with variations in temperature of the sample, especially for real-time and/or in situ applications where the sample temperature may vary over a wide range. More specifically, characteristics of the thin dielectric, such as its thickness, are not measured directly from the optical data but must be determined via model calculations. The results obtained depend on the values of many parameters assumed in the model, such as the substrate index of refraction and extinction coefficient. Unfortunately, the substrate index of refraction and extinction coefficient depend in turn on the temperature of the substrate. Hence, if the substrate temperature is not accurately known, the thickness calculation cannot be accurately performed. In fact, the thickness determination can be affected by unknown temperatures variations by as much as 0.01 angstroms per degree centigrade. Because wafers undergo wide temperature variations during processing, a simultaneous knowledge of the temperature of the wafer is critical for accurately and repeatably determining the thickness of the dielectric layer.

One simple method of dealing with this problem is to allow the wafer to cool to room temperature prior to measurement. However, this approach is time consuming. It would be far better to be able to determine the temperature of the wafer directly and take that temperature into account when evaluating the film thickness. Moreover, since the wafer might not cool uniformly or reproducibly, it would be very desirable to know the temperature of the wafer at the point at which the thickness is being measured.

In the prior art, it has been recognized that ellipsometric measurements can provide information simultaneously about the temperature and oxide-thickness of a sample. Such work is reported in "Ellipsometric Monitoring and Control of the Rapid Thermal Oxidation of Silicon," Conrad, et. al, Journal of Vacuum Science Technology B 11(6) November/December 1993. In this paper, the authors describe using a rotating analyzer ellipsometer (RAE) with a fixed compensator to take measurements from which the ellipsometric parameters $\psi$ and $\Delta$ can be calculated. From this information, the authors were able to derive information about temperature and film thickness.

A conventional RAE of the type used by the authors includes a polarizer that is rotated at an angular velocity omega ($\omega$)). Output signals at twice the rotation frequency ($2\omega$) are generated in both sine and cosine phases.

An RAE is an incomplete polarimeter, i.e., one that cannot measure all three Stokes parameters. As conventionally operated, i.e., without a compensator, the RAE cannot measure $S_3$, which describes circularly polarized light. Unfortunately, under the most favorable operating conditions, i.e., using HeNe laser illumination, the thickness of very thin oxide layers on Si affects only $S_3$. To overcome this limitation, a quarter-wave plate is used to convert the circularly polarized component to linear polarization, to which the RAE can respond. This is the approach adopted by Conrad et al. While this strategy allowed Conrad et al. to determine thickness and temperature simultaneously, being an incomplete polarimeter the RAE remains susceptible to systematic errors, such as depolarization, that could be detected in a complete polarimeter such as a rotating compensator ellipsometer (RCE). A second class of systematic error that can affect an RAE but not a RCE is connected to the fact that the detector must measure an intensity whose polarization is continuously changing with time, as a result of the rotating polarizer.

Accordingly, it would be highly desirable to provide a measurement system which could simultaneously and independently measure both temperature and thickness while avoiding the systematic errors that can occur with a RAE.

SUMMARY OF THE INVENTION

In accordance with these and other objects, the subject invention provides for an ellipsometer system that permits the simultaneous independent measurement, with equivalent accuracy, of both temperature and film thickness for relatively thin films. Using this system, variations in thickness measurements due to unknown temperature variations can be minimized leading to more accurate and repeatable results.

To achieve this goal, an RCE is used. In such a system, the rotating element is a birefringent element rather than polarizer as used in an RAE. It is well known that an RCE is capable of generating both $2\omega$ and $4\omega$ omega signals. It was discovered by the inventors herein that at least for relatively thin films (less than about 100 Angstroms), on a silicon substrate using a helium neon probe beam at 633 nm, the $4\omega$ signal varies in response to the temperature of the sample and is substantially independent of thin film thickness. On the other hand, the $2\omega$ signal varies in response to layer thickness and is substantially independent of temperature. By using the $4\omega$ signal, the temperature of the sample can be determined. The temperature of the sample can be used to determine the refractive index and extinction coefficient of the substrate and with that knowledge, the thin film thickness can be accurately determined using the $2\omega$ signal.

The subject invention has particular utility in a system wherein samples are measured after being subjected to processing steps that include heating the sample. Using this approach, accurate thickness measurements can be made without having to wait long periods for the wafer to cool to room temperature.

DESCRIPTION OF THE PREFERRED EMBODIMENT

Figure 1:
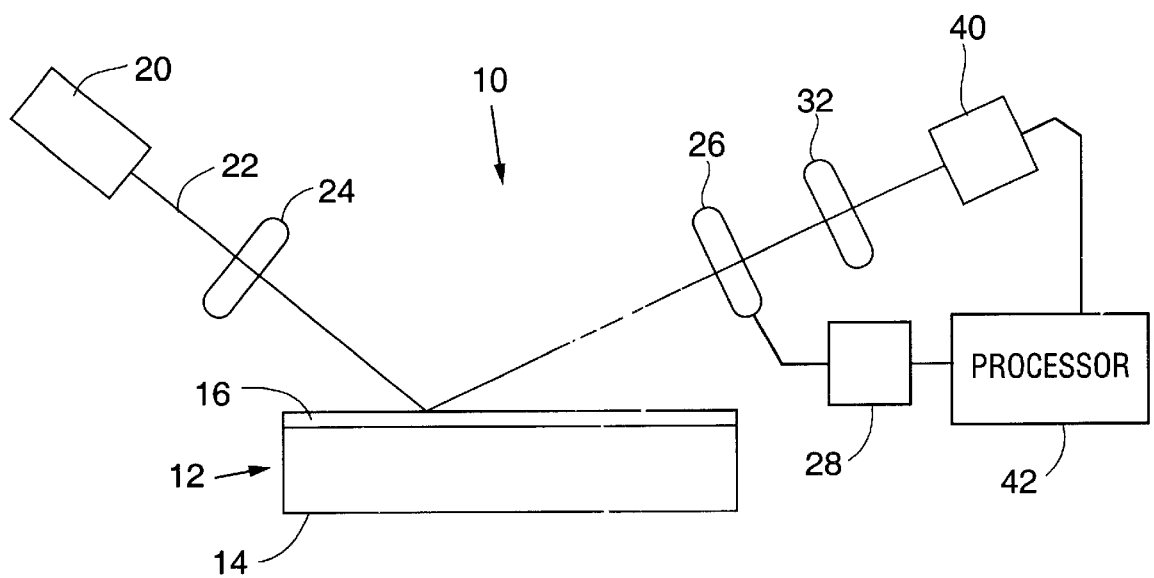
FIG. 1 is a schematic diagram of a rotating compensator ellipsometer.

Referring to FIG. 1, there is illustrated a rotating compensator ellipsometer 10 shown in position to measure characteristics of a sample 12. The sample 12 consists of a substrate 14 such as silicon. One or more thin films 16 are formed on the upper surface of the substrate.

The ellipsometer 10 includes a light source 20 for emitting a probe beam of radiation 22. In one preferred embodiment, light source 20 is a helium neon laser emitting a monochromatic beam at 633 nm. The advantage to a helium neon laser is that it generates a collimated beam of light of a known fixed wavelength which, in an ellipsometer configuration, substantially minimizes alignment, calibration, and measurement problems. It should be noted, however, the subject invention can be implemented with other light sources, including solid state lasers or laser diodes. It should also be noted that one advantage of this approach is that light in the visible region (greater than about 450 nm) can be used successfully to perform the measurements.

In addition, a polychromatic light source could be used with a monochrometer for scanning the wavelength. Alternatively, all wavelengths from the broadband source could be detected simultaneously as disclosed in U.S. Pat. No. 5,877,859, assigned to the same assignee herein and incorporated by reference.

The probe beam 22 passes through and interacts with a polarizer 24 to create a known polarization state. In the preferred embodiment, polarizer 24 is a linear polarizer made from a quartz Rochon prism, but in general the polarization does not necessarily have to be linear, nor even complete. Polarizer 24 can also be made from magnesium fluoride or calcite. The azimuth angle of polarizer 24 is oriented so that the plane of the electric vector associated with the linearly polarized beam exiting from the polarizer 24 is at a known angle with respect to the plane of incidence (defined by the propagation direction of the beam 22 and the normal to the surface of sample 12). The azimuth angle is preferably selected to be on the order of 30 degrees because the sensitivity is optimized when the reflected intensities of the P and S polarized components are approximately balanced. It should be noted that polarizer 24 can be omitted if the light source 20 emits light with the desired known polarization state.

The beam 22 is directed to sample 12 at an oblique angle. The beam 22 is ideally incident on sample 12 at an angle of the order of 70 degrees to the normal of the sample surface because sensitivity to sample properties is maximized in the vicinity of the Brewster or pseudo-Brewster angle of a material. Based upon well-known ellipsometric principles, the reflected beam will generally be in a mixed linear and circular polarization state after interacting with the sample, as compared to the linear polarization state of the incoming beam.

The reflected beam 22 passes through a rotating compensator (retarder) 26, which introduces a relative phase delay δ (phase retardation) between a pair of mutually orthogonal polarized optical beam components. The amount of phase retardation is a function of the wavelength, the dispersion characteristics of the material used to form the compensator, and the thickness of the compensator. Compensator 26 is rotated at an angular velocity omega (ω) about an axis substantially parallel to the propagation direction of beam 22, preferably by an electric motor 28. Compensator 26 can be any conventional wave-plate compensator, for example those made of crystal quartz. The thickness and material of the compensator 26 are selected such that a desired phase retardation of the beam is induced. In the preferred embodiment, compensator 26 is a bi-plate compensator constructed of two parallel plates of anisotropic (usually birefringent) material, such as quartz crystals of opposite handedness, where the fast axes of the two plates are perpendicular to each other and the thicknesses are nearly equal, differing only by enough to realize a net first-order retardation for the wavelength produced by the light source 20.

Beam 22 then interacts with analyzer 32, which serves to mix the polarization states incident on it. In this embodiment, analyzer 32 is another linear polarizer, preferably oriented at an azimuth angle of 45 degrees relative to the plane of incidence. However, any optical device that serves to appropriately mix the incoming polarization states can be used as an analyzer. The analyzer 32 is preferably a quartz Rochon or Wollaston prism but, as noted above, could also formed from magnesium fluoride or calcite.

The rotating compensator 26 changes the polarization state of the beam as it rotates such that the light transmitted by analyzer 32 is characterized by:

$$I(t) = (1/2)[|E_x|^2(1 + \cos^2(\delta/2) + |E_y|^2\sin^2(\delta/2)] - \quad (1)$$
$$\mathrm{Im}(E_x E_y^*)\sin\delta\sin(2\omega t) +$$
$$\mathrm{Re}(E_x E_y^*)\sin^2(\delta/2)\sin(4\omega t) +$$
$$(1/2)(|E_x|^2 - |E_y|^2)\sin2(\delta/2)\cos(4\omega t)$$
$$= a_o + b_2\sin(2\omega t) + a_4\cos(4\omega t) + b_4\sin(4\omega t),$$

where $E_x$ and $E_y$ are the projections of the incident electric field vector parallel and perpendicular, respectively, to the transmission axis of the analyzer, δ is the phase retardation of the compensator, and ω is the angular rotational frequency of the compensator.

For linearly polarized light reflected at non-normal incidence from the specular sample, we have $$E_x = r_p \cos P$$
$$E_y = r_s \sin P \quad (2)$$

where the transmission axis of the analyzer is assumed to be in the plane of incidence, and P is the azimuth angle of the transmission axis of the polarizer with respect to the plane of incidence. The coefficients $a_0$, $b_2$, $a_4$, and $b_4$ can be combined in various ways to determine the complex reflectance ratio:

$$r_p/r_s = \tan\psi e^{i\Delta}. \quad (3)$$

It should be noted that the compensator 26 can be located either between the sample and the analyzer 32 (as shown in FIG. 1), or between the sample and the polarizer 24, with appropriate and well known minor changes to the equations. It should also be noted that the polarizers and compensator are all optimized in their construction for the specific wavelength of light produced by light source 20, which maximizes the accuracy of ellipsometer.

Beam 22 then enters detector 40, which measures the intensity of the beam passing through the compensator/analyzer combination. The processor 42 processes the intensity information measured by the detector 40 to determine the polarization state of the light after interacting with the analyzer, and therefore the ellipsometric parameters of the sample. This information processing includes measuring beam intensity as a function of the azimuth (rotational) angle of the compensator about its axis of rotation. This measurement of intensity as a function of compensator rotational angle is effectively a measurement of the intensity of beam 22 as a function of time, since the compensator angular velocity is usually known and a constant. As can be seen from equation (1), a rotating compensator will generate a signal having a dc. component, a $2\omega$ signal and a $4\omega$ signal with respect to the rotation rate of the compensator.

It should be noted that the compensator need not be continuously rotating, but can be rotated incrementally with measurements being taken at each rotational position. Even if the compensator is rotated incrementally, the output can still be analyzed in the form of $2\omega$ and $4\omega$ signals.

It is convenient to recast Equation (1) in terms of normalized Fourier coefficients $\beta_2$, $\alpha_4$, and $\beta_4$ defined as $$I = I_0[1 + \beta_2 \sin 2\omega t + \alpha_4 \cos 4\omega t + \beta_4 \sin 4\omega t], \quad (4)$$

since these are the coefficients that can be determined most accurately experimentally, e.g., by a normalized harmonic analysis of the detected photoelectric current from detector 40. For our purposes we need only relative intensities, whence it is useful to define a relative amplitude $\tan \psi'$ and a relative phase $\Delta'$ of the two field components such that $\tan \psi' \exp(i\Delta') = E_y/E_x$. In terms of $\psi'$ and $\Delta'$ we have $$\beta_2 = [\sin \Delta' \sin \delta \sin 2\omega']/D;$$

$$\alpha_4 = [\sin^2(\delta/2) \cos 2\omega']/D;$$

$$\beta_4 = [\cos \Delta' \sin^2(\delta/2) \sin 2\omega']/D; \quad (5)$$

where $$D = [1 + \cos^2(\delta/2)] \cos^2 \omega' + \sin^2(\delta/2) \sin^2 \omega'.$$

As mentioned above, we have discovered that the signals generated by the RCE can be used to measure essentially independently the temperature of a sample and the thickness of a thin film formed thereon. This independence arises from the nature of the two different signals. More specifically, for very thin films, the $2\omega$ signal is essentially proportional to the phase shift $\Delta'$, which in turn is most affected by the thickness of the thin film. Unfortunately, this signal is also somewhat affected by the refractive index and extinction coefficient of the substrate, which also vary with temperature. As noted above, unknown variations in temperature can effect a thickness measurement by as much as 0.01 angstroms per degree centigrade. Where measurements are consistently taken at room temperature, the latter effect can be ignored. However, if the temperature of the wafer is unknown, the variations in refractive index and extinction coefficient can create measurement errors.

The inventors herein have recognized that the $4\omega$ signal generated by the RCE can be used to independently determine temperature. More specifically, the $4\omega$ coefficient $\alpha_4$ is completely independent of $\Delta$, and for thin transparent films on Si at wavelengths longer than about 450 nm, $\Delta \cong \pm 1$, whence $\beta_4$ is also essentially independent of $\Delta$. Then both $\alpha_4$ and $\beta_4$ will be determined by the complex refractive index n of the substrate. Since the index of refraction of a sample is highly temperature dependent, changes in temperature of the substrate will vary the index of refraction and hence $\psi$. These changes in $\psi$ are directly detected in the $4\omega$ signal of an RCE.

We provide a quantitative description as follows. To first order in $d/\lambda$, where d is the film thickness and $\lambda$ is the wavelength of light, we have:

$$\tan \psi' e^{i\Delta'} = \rho_o \left\{ 1 + \frac{4\pi i d \cos \theta}{\lambda} \frac{\varepsilon_s(\varepsilon_s - \varepsilon_0)(\varepsilon_0 - \varepsilon_a)}{\varepsilon_0(\varepsilon_s - \varepsilon_a)(\varepsilon_s \cot^2 \theta - \varepsilon_a)} \right\} \quad (6)$$

where $\varepsilon_s$, $\varepsilon_0$, and $\varepsilon_a$ are the dielectric functions of the substrate, overlayer, and ambient, respectively, $\theta$ is the angle of incidence, and $$\rho_o = \frac{\sin^2 \theta - \cos \theta \sqrt{\varepsilon_s/\varepsilon_a - \sin^2 \theta}}{\sin^2 \theta - \cos \theta \sqrt{\varepsilon_s/\varepsilon_a - \sin^2 \theta}} \quad (7)$$

The refractive indices $n_s$, $n_0$, and $n_a$ are related to $\varepsilon_s$, $\varepsilon_0$, and $\varepsilon_a$ by $n_s^2 = \varepsilon_s$, $n_0^2 = \varepsilon_0$, and $n_a^2 = \varepsilon_a$. Generally $n_a^2 = \varepsilon_a = 1$.

For Si using a HeNe probe at 632.8 nm, we have $\varepsilon_s = 15.068 + i0.150$, which is nearly real. Since for a transparent overlayer $\varepsilon_0$ is real, it follows that both $\rho_o$ and the coefficient multiplying $4\pi i d \cos \theta/\lambda$ are also nearly real. For small $d/\lambda$ it follows therefore that $$\Delta' \cong \frac{4i\pi d \cos \theta}{\lambda} \frac{\varepsilon_s(\varepsilon_s - \varepsilon_0)(\varepsilon_0 - \varepsilon_a)}{\varepsilon_0(\varepsilon_s - \varepsilon_a)(\varepsilon_s \cot^2 \theta - \varepsilon_a)}, \quad (8)$$

which shows that $\Delta'$ is essentially linearly proportional to d. It further follows that to first order in $d/\lambda$ $$\tan \psi' = \rho_O$$

is independent of d and therefore depends only on the temperature (through the temperature dependence of $\varepsilon_s$). Continuing, since the coefficient of $4\pi i d \cos \theta/\lambda$ depends on $\varepsilon_s$, it follows that the accurate determination of d requires a knowledge of T.

The above discussion can be made more rigorous by considering higher order terms or using the exact expressions. However, the main conclusions that the $4\omega t$ terms should depend essentially entirely on temperature and the $2\omega t$ term depends mainly on d but exhibits a weak dependence on temperature follow from the first-order expression and this dependence has been confirmed experimentally.

Figure 2A:
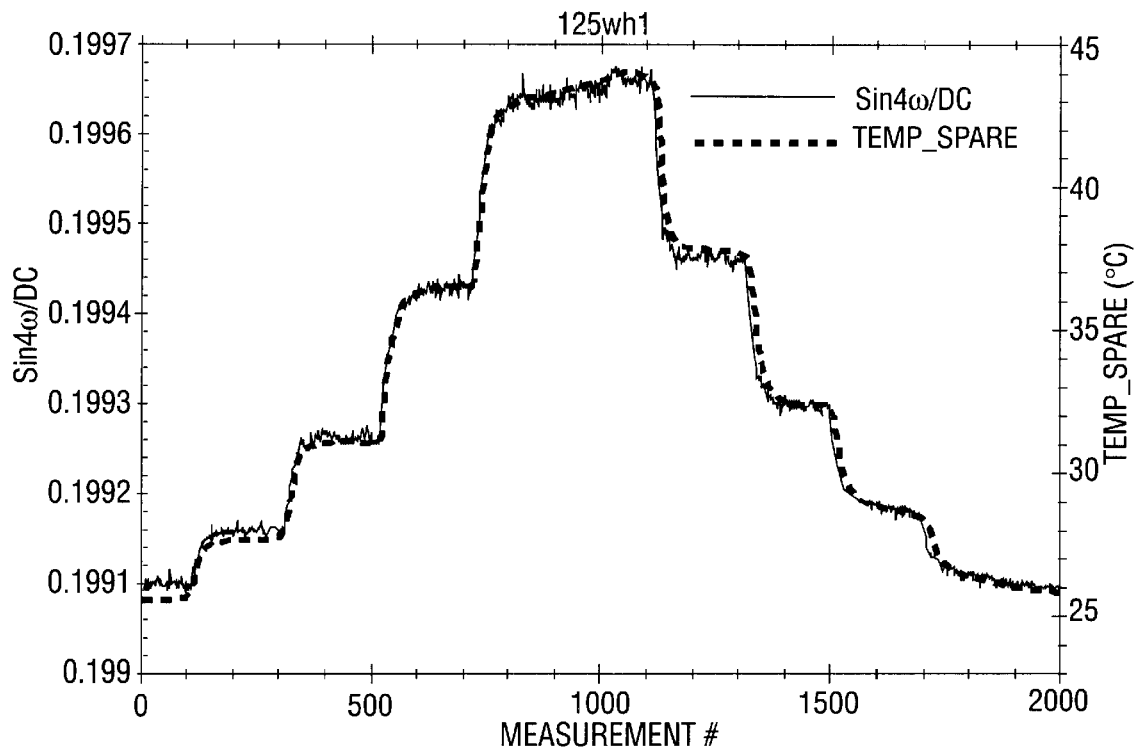
FIGS. 2a and 2b are graphs illustrating the variation of the sine and cosine $4\omega$ signals with temperature.
Figure 2B:
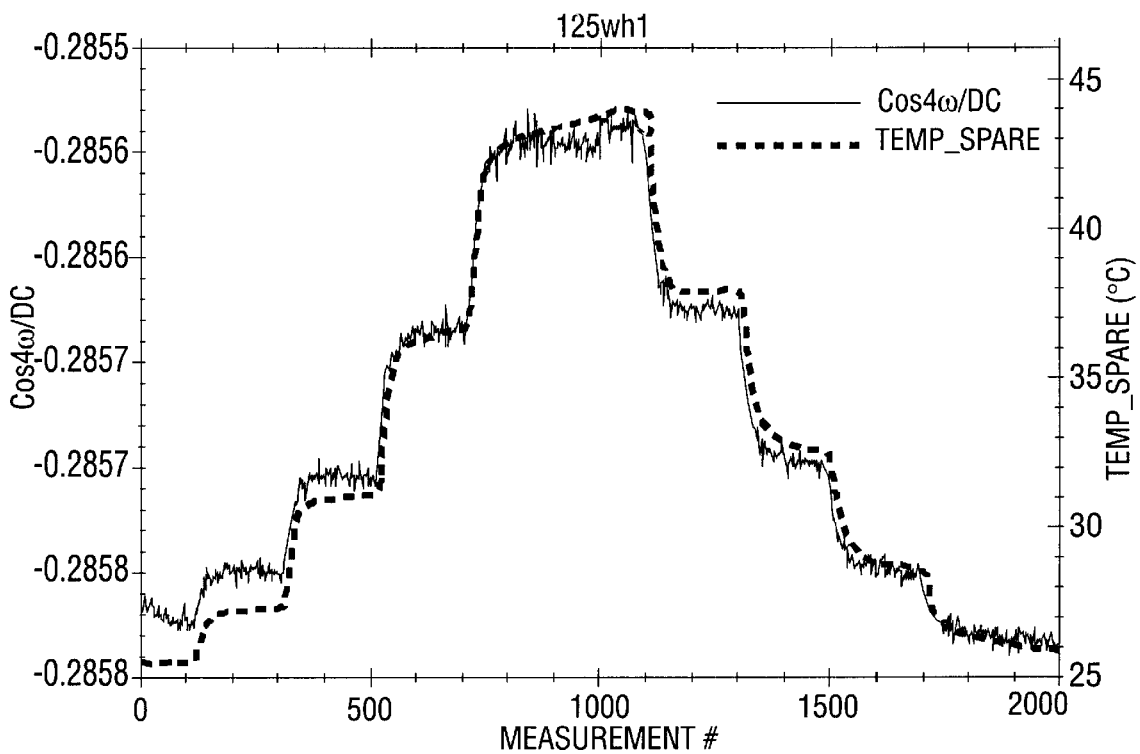

This dependence of the $4\omega$ signal is shown experimentally in FIG. 2. FIG. 2a illustrates the variation of the sin $4\omega$ signal with temperature while FIG. 2b illustrates the variation of the cos $4\omega$ signal with temperature. As can be seen, both signals track the temperature quite well, with the sin $4\omega$ signal virtually overlapping the plot of temperature variations. The signal-to-noise capability is such that differences of 1° C. can be readily observed. In these experiments, the sample is a bare silicon wafer heated by contact heaters. The temperature was monitored by an attached thermistor at the wafer surface.

In practice, plots of the sort shown in FIG. 2 would be generated for particular types of samples. A table would be created mapping one or both of the $4\omega$ signals to an actual measured temperature. Thereafter, when a production sample is being tested, the $4\omega$ signal obtained by the RCE can be compared to the table to determine the temperature of the wafer.

Once the temperature of the wafer is known, the coefficient of $d/\lambda$ in Eq. (6) can be determined. This information can be used to correct the thickness measurement made using the 2ω signal.

Figure 3A:
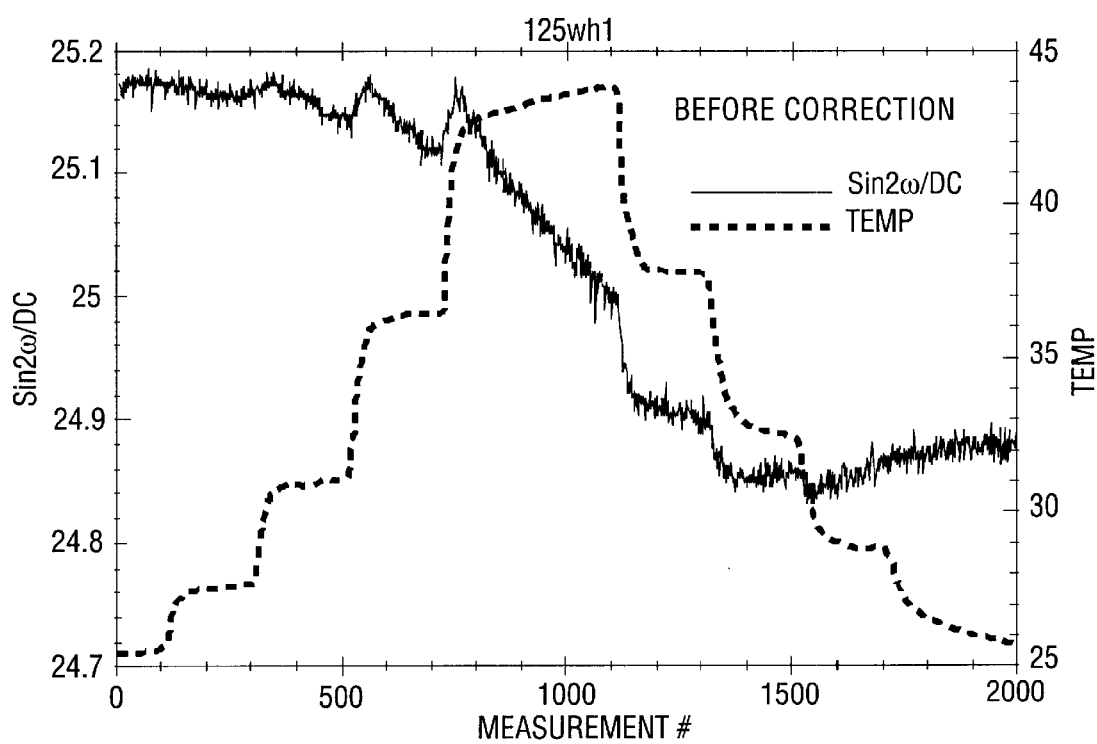
FIG. 3a is a graph illustrating the variation of the sin 2ω signal with temperature.
Figure 3B:
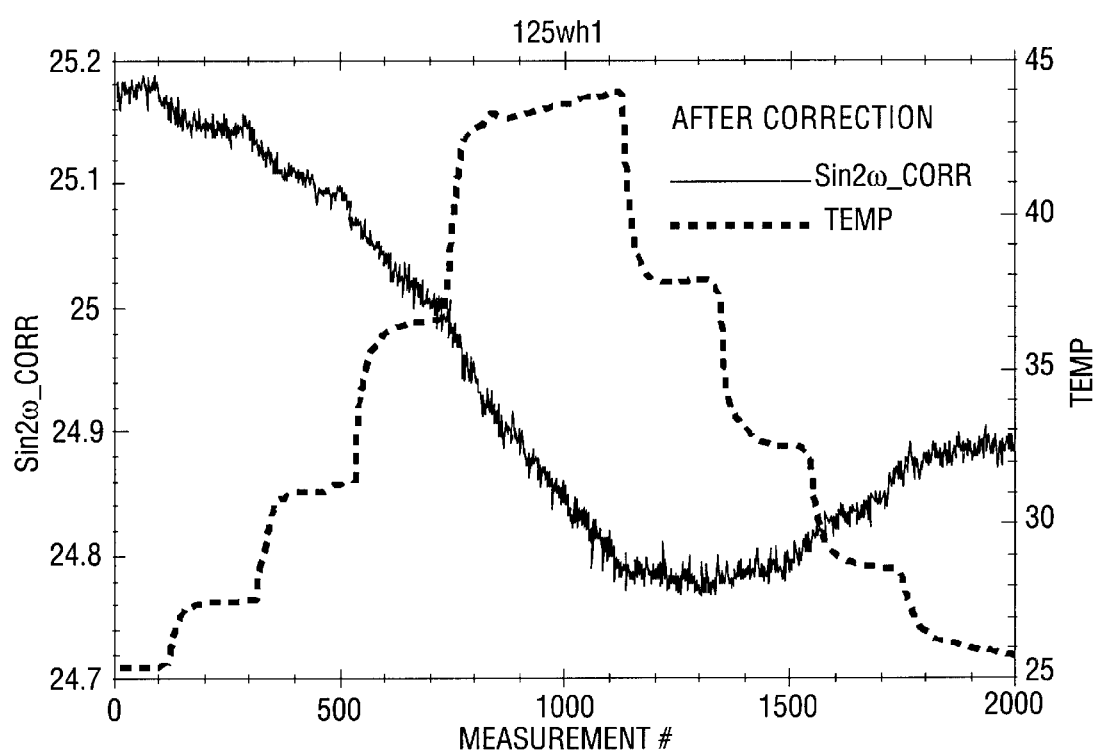
FIG. 3b is a graph illustrating the variation of the sin 2ω signal after it has been corrected with the data from the 4ω signal.

FIG. 3a illustrates the sin 2ω signal generated by the RCE as the temperature is varied. As can be seen, there are many peaks and sharp drops. In FIG. 3b, this sin 2ω signal has been corrected using the sin 4ω signal on the basis of the equation given above and as described below. As can be seen, the sin 2ω signal now varies smoothly with the temperature variation. This variation represents actual changes in thickness due to absorption and desorption of contaminants under changing temperature. Such variations can be minimized if measurements are taken in a vacuum chamber.

The sin 2ω signal in FIG. 3b was corrected by the sin 4ω signal using the following expression:

$$(\text{Sin } 2\omega)_{corrected} = (\text{Sin } 2\omega)_{measured} - c(T-T_0)$$

where $T$ and $T_0$ are the wafer temperature at the measurement and at the reference condition, respectively; and $c$ is the temperature coefficient of sin 2ω, derived from the theoretical film/substrate model substituting in the relationship of $k_s = k_s(T)$, where $k_s$ is the extinction coefficient of the substrate.

The temperature difference $(T-T_0)$ in the above equation is determined from the 4ω signal in the same measurement:

$$(T-T_0) = [(4\omega)_{measured} - (4\omega)_0]/b$$

where $b$ is the temperature coefficient of 4ω obtained from a temperature calibration experiment (as shown in FIG. 2) by fitting $4\omega = a + b\,T$. The coefficient $b$ can be accurately determined because of the sole dependency of 4ω on temperature. In other words, the value of 4ω is not affected by the sub-angstrom thickness variation, as shown by Eq. (6) and also seen from the sin 2ω signal of the film during the temperature calibration process.

It is envisioned that this system will find utility measuring thin films, such as gate dielectrics on substrates either in situ or between processing steps where the wafer has not yet cooled. If used in situ, the probe beam could be directed into a process chamber directly onto the surface of the wafer as the dielectric layer was being formed. The 4ω signal could be used to monitor the temperature of the wafer while the 2ω signal could be used to monitor the change in thickness of a the layer during processing.

Similarly, if the wafer has just been removed from a process chamber, it could be placed in the RCE measurement module. The 4ω signal could be used to derive the change in temperature during the cool down phase and provide a correction of the thickness measurement based on the 2ω signal. In order to improve accuracy, a number of thickness measurements could be made at different temperatures.

It is believed that a single wavelength system, using for example, a helium neon laser should provide good results for single layer thin film samples. For more complex samples, it may be desirable to use a spectroscopic rotating compensator ellipsometer. As noted above, one suitable spectroscopic RCE is described in U.S. Pat. No. 5,877,859.

While the subject invention has been described with reference to a preferred embodiment, various changes and modifications could be made therein, by one skilled in the art, without varying from the scope and spirit of the subject invention as defined by the appended claims.

We claim:

1. A method of evaluating a sample having a thin film formed on a substrate utilizing the output of a rotating compensator ellipsometer (RCE), said RCE generating two omega and four omega output signals, said method comprising the steps of:

monitoring both the two omega and four omega output signals;

determining the temperature of the sample based on the four omega signals; and determining the thickness of the thin film on the substrate based on the two omega signal and the previously determined temperature of the, sample.

2. A method of evaluating a sample having a thin film formed on a substrate utilizing the output of a rotating compensator ellipsometer (RCE), said RCE generating two omega and four omega output signals, said method comprising the steps of:

monitoring both the two omega and four omega output signals; and determining the thickness of the thin film on the substrate based on the two omega output signals and wherein said thickness determination includes an evaluation of the temperature dependent index of refraction of the sample based on the four omega output signals.

3. An apparatus for evaluating a sample having a thin film formed on a substrate comprising:

a light source for generating a probe beam of radiation having a known polarization state directed to reflect off the sample at a non-normal angle of incidence;

an analyzer for determining the change in polarization state of the beam upon reflection from the sample, said analyzer including a compensator which is rotatable at an angular velocity omega and wherein said analyzer generates output signals at two omega and four omega; and a processor for evaluating the sample based on the output signals generated by the analyzer, said processor utilizing the four omega signal to provide information about the temperature of the sample and the two omega signal to provide information about the thickness of the thin film.

4. An apparatus as recited in claim 3, wherein said light source is a laser.

5. An apparatus as recited in claim 4, wherein said laser is a helium neon laser.

6. An apparatus for evaluating a sample having a thin film formed on a substrate comprising:

a rotating compensator ellipsometer for generating an output including both two omega and four omega signals; and a processor for evaluating the sample based on the output signals generated by the analyzer, said processor utilizing the four omega signal to provide information about the temperature of the sample and the two omega signal to provide information about the thickness of the thin film.

7. An apparatus for evaluating a sample having a thin film formed on a substrate comprising:

a rotating compensator ellipsometer for generating an output including both two omega and four omega signals; and a processor for determining the thickness of the thin film on the substrate based on the two omega output signals and wherein said thickness determination includes an evaluation of the temperature dependent index of refraction of the sample derived from the four omega output signals.

8. A method of evaluating a sample which has been subjected to a processing step which included heating the sample, said sample having a thin film formed on a substrate, said method utilizing the output of a rotating compensator ellipsometer (RCE), said RCE generating two omega and four omega output signals, said method comprising the steps of:

monitoring the four omega signal to provide information about the variations in temperature of the sample; and monitoring the two omega signal to provide information about the thickness of the thin film at a different temperature.

9. A method of evaluating a sample which is located in a deposition chamber where a thin film is being deposited on a substrate at an elevated temperature, said method utilizing the output of a rotating compensator ellipsometer (RCE), said RCE generating two omega and four omega output signals, said method comprising the steps of:

monitoring the four omega signal to provide information about the variations in temperature of the sample; and monitoring the two omega signal to provide information about the growth of the film thickness wherein said thickness determination includes temperature information derived from the four omega output signals.

10. A method of evaluating a sample which has been subjected to a processing step which included heating the sample, said sample having a thin film formed on a substrate, said method utilizing the output of a rotating compensator ellipsometer (RCE), said RCE generating two omega and four omega output signals, said method comprising the steps of:

monitoring the two and four omega output signals; and determining the thickness of the thin film on the substrate based on the two omega output signals and wherein said thickness determination includes an evaluation of the temperature dependent index of refraction of the sample based on the four omega output signals.

11. A method of evaluating a sample which is located in a deposition chamber where a thin film is being deposited on a substrate at an elevated temperature, said method utilizing the output of a rotating compensator ellipsometer (RCE), said RCE generating two omega and four omega output signals, said method comprising the steps of.

monitoring the two and four omega output signals; and evaluating the growth of the film thickness on the substrate based on the two omega output signals and wherein said thickness determination includes an evaluation of the temperature dependent index of refraction of the sample based on the four omega output signals.

* * * * *